(12) United States Patent
Rannikko et al.

(10) Patent No.: US 7,521,244 B2
(45) Date of Patent: Apr. 21, 2009

(54) STANDARD REFERENCE SOLUTIONS

(75) Inventors: Minna A. Rannikko, Millbury, MA (US); Donna Connors, Gardner, MA (US); Donna Rafferty, Ashburnham, MA (US)

(73) Assignee: Bionostics, Inc., Devens, MA (US)

( * ) Notice: Subject to any disclaimer, the term of this patent is extended or adjusted under 35 U.S.C. 154(b) by 209 days.

(21) Appl. No.: 11/588,160

(22) Filed: Oct. 26, 2006

(65) Prior Publication Data

US 2008/0102525 A1  May 1, 2008

(51) Int. Cl.
*G01N 31/00* (2006.01)
*G01N 33/72* (2006.01)

(52) U.S. Cl. .............. 436/15; 436/8; 436/14; 436/18; 436/63; 436/66; 436/67; 436/95; 436/86; 436/87; 435/14; 252/408.1

(58) Field of Classification Search ........ 436/8, 436/14, 15, 18, 63, 66, 67, 95, 98, 128, 86, 436/87; 435/2, 14; 252/408.1
See application file for complete search history.

(56) References Cited

U.S. PATENT DOCUMENTS

| | | | | |
|---|---|---|---|---|
| 3,964,865 A | * | 6/1976 | Das .............. | 436/66 |
| 3,977,995 A | * | 8/1976 | Louderback et al. ......... | 436/10 |
| 4,260,516 A | * | 4/1981 | Moore ........... | 436/15 |
| 4,274,978 A | * | 6/1981 | Moore ........... | 436/15 |
| 4,465,774 A | * | 8/1984 | Huang et al. ........ | 436/15 |
| 4,590,164 A | * | 5/1986 | Gain ............. | 436/15 |
| 5,132,230 A | * | 7/1992 | Rosenthal et al. .......... | 436/15 |
| 5,580,794 A | | 12/1996 | Allen | |
| 5,589,393 A | * | 12/1996 | Fiechtner et al. .......... | 436/15 |
| 5,837,546 A | | 11/1998 | Allen et al. | |
| 6,372,503 B1 | * | 4/2002 | Samsoondar .......... | 436/8 |
| 6,900,058 B2 | * | 5/2005 | Rannikko et al. .......... | 436/14 |
| 7,361,513 B2 | * | 4/2008 | Ryan et al. .......... | 436/67 |
| 2004/0180444 A1 | | 9/2004 | Rannikko et al. | |
| 2005/0175977 A1 | * | 8/2005 | Posner et al. .......... | 435/2 |

FOREIGN PATENT DOCUMENTS

WO    199747972    12/1997

OTHER PUBLICATIONS

Nakanishi et al. Clinical Chemistry, vol. 49, No. 5, 2003, pp. 829-831.*
Goldstein, et al., Clin. Chem.. Glycated Hemoglobin: Methodologies and Clinical Applications, 32:/10(b), B64-B70, 1986.
Mayer et al., Clin. Chem. Acta, Protein Glycosylation in Diabetes Mellitus: A Review of Laboratory Measurements and of their Clinical Utility; 127:147-184, 1983.

(Continued)

*Primary Examiner*—Maureen M Wallenhorst
(74) *Attorney, Agent, or Firm*—McDermott Will & Emery LLP (57) ABSTRACT

Standard reference materials and related methods are described for quality testing and calibration of instruments used for the qualitative and quantitative determination of hemoglobin and glycated hemoglobin as well as other analytes of interest in animal tissue samples. The reference solutions of the disclosure utilize a synthetic cruor in combination with an Hb peptide chain.

15 Claims, 3 Drawing Sheets

OTHER PUBLICATIONS

Fluckiger, et al., Journ. Of Chromatography, Glycated Haemoglobins, 429: 279-292, 1988.

Goldstein, et al., CRC Critical Review Clin. Lab. Sci., Recent Advances in Glycosylated Hemoglobin Measurements, 21:187-228, 1984.

Peacock, J. Clin. Pathol., Glycosylated Haemoglobin: Measurement and Clinical Use, 37:841-851, 1984.

Lester, Ann. Clin. Biochem, The Clinical Value of Glycated Haemoglobin and Glycated Plasma Proteins, 26:213-219, 1989.

Miedema, et al., Ann. Clin. Biochem, Glycosylated Haemoglobins, Biochemical Evaluation and Clinical Utility, 21:2-15, 1984.

Mortensen, Danish Med. Bulletin, Glycated Hemoglobin, 32:309-328, 1985.

Hoelzel, et al., Clinical Chem, IFCC Reference System for Measurement of Hemoglobin A1c in Human Blood and the National standarziation Schemes in the United Staes, Japan, and Sweden: A Method-Comparison Study, 50:166-174, 2004.

Kennedy, et al., British Med. Bull., Non-Enzymatic Glycosylation, 45:174-190, 1989.

Gabbay, Med. Clinics of N. America, Glycosylated Hemoglobin and Diabetes Mellitus, 66:1309-1315, 1982.

Blumberg, W., e al., "Hemo Globin Determined in 15 Microliters of Whole Blood by Front Face Fluorometry", Clinical Chemistry, vol. 26, No. 3, 1980, pp. 409-413.

Nakanishi, T., et al., "Method for Hemoglobin A1c Measurement Based on Peptide Analysis by Electrospray Ionization Mass Spectrometry with Deuterium-labeled Synthetic Peptides as Internal Standards", Clinical Chemistry, vol. 49, No. 5, 2003, pp. 829-831.

Kobuld, U., et al., "Candidate Reference Methods for Hemoglobin A-1c Based on Peptide Mapping", Clinical Chemistry, American Association for Clinical Chemistry, vol. 43, No. 10, Jan. 1, 1997, pp. 1944-1951.

International Search Report for Corresponding PCT Application No.: PCT/US07/082620, 5PP.

Written Opinion for Corresponding PCT Application No.: PCT/US07/082620, 7PP.

* cited by examiner

Bionostics lot x40204C Level 1 Time Zero

|  | Microalbumin | Creatinine | Glucose | BHY (Ketone) | Hb | HbA1c | %HbA1c |
|---|---|---|---|---|---|---|---|
|  | (mg/L) | (mg/dL) | (mg/dL) | (mM) | (umol/L) | (umol/L) | (%) |
|  | 13.8 | 28.5 | 89 | 0.96 | 151 | 415 | 6.9 |
|  | 14.1 | 27.9 | 89 | 0.99 | 149 | 411 | 6.9 |
|  | 13.3 | 26.1 | 85 | 0.96 | 152 | 436 | 7.1 |
|  | 13.4 | 26.0 | 85 | 0.99 | 158 | 403 | 6.5 |
|  | 13.1 | 27.0 | 86 | 0.96 | 157 | 412 | 6.7 |
|  | 13.3 | 28.1 | 82 | 0.99 | 158 | 407 | 6.6 |
|  | 13.2 | 27.4 | 87 | 0.97 | 150 | 388 | 6.6 |
|  | 12.8 | 27.8 | 87 | 0.99 | 155 | 380 | 6.3 |
|  | 12.2 | 26.6 | 88 | 0.96 | 157 | 385 | 6.3 |
|  | 12.9 | 28.1 | 89 | 0.98 | 158 | 403 | 6.5 |
|  | 13.1 | 28.4 | 84 | 1.00 | 154 | 388 | 6.5 |
|  | 12.7 | 27.5 | 83 | 0.96 | 158 | 394 | 6.4 |
|  | 13.7 | 27.8 | 91 | 0.96 | 159 | 391 | 6.4 |
|  | 12.3 | 27.3 | 90 | 0.97 | 157 | 395 | 6.5 |
|  | 11.6 | 28.5 | 89 | 0.97 | 158 | 391 | 6.4 |
|  | 13.4 | 30.4 | 90 | 0.99 | 160 | 391 | 6.3 |
|  | 12.3 | 29.4 | 87 | 1.01 | 159 | 408 | 6.6 |
|  | 12.9 | 27.1 | 88 | 0.99 | 158 | 414 | 6.7 |
|  | 12.5 | 27.9 | 87 | 0.98 | 161 | 418 | 6.6 |
|  | 11.9 | 29.8 | 87 | 0.99 | 160 | 399 | 6.4 |
|  | 12.0 | 26.3 | 86 | 0.99 | 160 | 415 | 6.6 |
|  | 12.3 | 26.7 | 88 | 1.00 | 166 | 427 | 6.6 |
|  | 12.1 | 27.7 | 85 | 0.89 | 164 | 411 | 6.5 |
|  | 12.1 | 27.9 | 88 | 0.99 | 162 | 394 | 6.3 |
|  | 12.2 | 26.2 | 87 | 0.99 | 159 | 414 | 6.6 |
|  | 11.5 | 26.7 | 84 | 0.97 | 157 | 397 | 6.5 |
|  | 12.0 | 26.4 | 89 | 0.99 | 155 | 402 | 6.6 |
|  | 12.4 | 27.9 | 83 | 0.98 | 158 | 410 | 6.6 |
|  | 12.6 | 27.4 | 83 | 0.99 | 157 | 396 | 6.5 |
|  | 12.2 | 28.5 | 85 | 0.97 | 156 | 391 | 6.4 |
| mean | 12.7 | 27.6 | 87 | 0.98 | 157 | 403 | 6.5 |
| sd | 0.7 | 1.1 | 2 | 0.02 | 4 | 13 | 0.2 |
| %CV | 5.2 | 3.9 | 3 | 2.23 | 2 | 3 | 2.7 |

FIG. 2B

Bionostics lot x40204D Level 2 Time Zero

|  | Microalbumin | Creatinine | Glucose | BHY (Ketone) | Hb | HbA1c | %HbA1c |
|---|---|---|---|---|---|---|---|
|  | (mg/L) | (mg/dL) | (mg/dL) | (mM) | (umol/L) | (umol/L) | (%) |
|  | 60.2 | 221.2 | 272 | 3.99 | 159 | 895 | 12.2 |
|  | 58.2 | 221.2 | 261 | 4.05 | 156 | 872 | 12.1 |
|  | 65.8 | 222.9 | 256 | 4.00 | 157 | 879 | 12.1 |
|  | 66.6 | 229.9 | 273 | 4.00 | 158 | 876 | 12.0 |
|  | 59.8 | 228.0 | 267 | 4.09 | 158 | 865 | 11.9 |
|  | 66.0 | 223.8 | 261 | 4.12 | 159 | 853 | 11.7 |
|  | 65.2 | 225.2 | 261 | 3.89 | 158 | 870 | 12.0 |
|  | 62.2 | 226.4 | 256 | 4.05 | 161 | 857 | 11.7 |
|  | 65.3 | 226.7 | 259 | 3.64 | 161 | 838 | 11.4 |
|  | 63.7 | 210.3 | 266 | 4.07 | 159 | 905 | 12.3 |
|  | 62.5 | 219.6 | 252 | 4.05 | 161 | 851 | 11.6 |
|  | 65.2 | 223.5 | 261 | 4.03 | 158 | 879 | 12.1 |
|  | 64.2 | 220.4 | 270 | 4.07 | 157 | 882 | 12.2 |
|  | 61.5 | 222.1 | 260 | 4.03 | 157 | 840 | 11.7 |
|  | 65.8 | 219.5 | 260 | 3.53 | 155 | 852 | 11.9 |
|  | 60.1 | 234.2 | 269 | 3.74 | 156 | 856 | 11.9 |
|  | 62.5 | 218.9 | 262 | 3.88 | 157 | 859 | 11.9 |
|  | 63.5 | 222.3 | 264 | 3.89 | 157 | 857 | 11.9 |
|  | 65.6 | 230.8 | 265 | 3.86 | 159 | 892 | 12.2 |
|  | 62.3 | 220.0 | 250 | 3.95 | 158 | 888 | 12.2 |
|  | 62.5 | 205.6 | 259 | 3.96 | 159 | 875 | 12.0 |
|  | 64.5 | 198.1 | 271 | 4.02 | 159 | 888 | 12.1 |
|  | 60.8 | 212.9 | 253 | 4.08 | 160 | 861 | 11.8 |
|  | 64.0 | 208.5 | 260 | 4.02 | 160 | 873 | 11.9 |
|  | 66.1 | 215.9 | 264 | 3.85 | 158 | 870 | 12.0 |
|  | 64.4 | 226.4 | 251 | 3.97 | 158 | 882 | 12.1 |
|  | 65.7 | 224.4 | 252 | 3.55 | 158 | 874 | 12.1 |
|  | 62.1 | 224.0 | 262 | 3.83 | 158 | 865 | 11.9 |
|  | 62.2 | 217.6 | 261 | 4.04 | 158 | 863 | 11.9 |
|  | 62.6 | 213.0 | 260 | 3.96 | 158 | 896 | 12.3 |
| mean | 63.4 | 220.4 | 261 | 3.94 | 158 | 870 | 12.0 |
| sd | 2.2 | 7.8 | 6 | 0.15 | 1 | 17 | 0.2 |
| %CV | 3.5 | 3.5 | 2 | 3.89 | 1 | 2 | 1.7 |

STANDARD REFERENCE SOLUTIONS

FIELD OF THE DISCLOSURE

This disclosure relates primarily to the field of clinical reference solutions, quality control reagents and calibrators. More particularly, the present disclosure relates to single reference solutions suitable for devices for the detection and/or quantitation of analytes found in animal tissues (e.g., inside red blood cells, plasma, and urine). The reference solutions of the disclosure utilize a synthetic cruor in combination with an Hb peptide chain.

BACKGROUND INFORMATION

Diabetes mellitus is a group of metabolic diseases characterized by chronic hyperglycemia, an increased blood sugar (glucose) levels. Glycated hemoglobin is a generic term referring to a series of minor hemoglobin components that are formed via the attachment of various sugars, most commonly glucose, to the hemoglobin molecule. The most important of these minor hemoglobin components in respect to diabetes is hemoglobin A1c (HbA1c). It is formed by the attachment of glucose to the N-terminal amino acid residue, valine, on one or both β chains of hemoglobin A. The determination of both total hemoglobin and HbA1c is recognized as clinically important in the diagnosis, monitoring, and control of diabetic patients (see e.g., Harrison's *Principles of Internal Medicine*, 16$^{th}$ ed., McGraw-Hill, New York, 2005).

Optimal therapy of diabetic patients requires also the evaluation of blood/plasma for various other analytes including for example glucose, ketone, microalbumin, creatine, urea and proteinuria markers (see e.g., Reinauer et al. 2002, World Health Organization "Laboratory Diagnosis and Monitoring of Diabetes Mellitus").

The determination of HbA1c and the percentage thereof in total hemoglobin are used in the measurement of the severity of glucose intolerance in a diabetic patient and in management of diabetes mellitus (Lester, Ann. Clin. Biochem. 26:213-219, (1989); Kennedy et al., Br. Med. Bull. 45:174-190, (1989); Fluckiger et al., J. Chromatogr. 429:279-292, (1988); Goldstein, et al., Clin. Chem. 32:B64-70, (1986); Mortensen, Dan. Med. Bull. 32:309-328, (1985); Goldstein et al., CRC Crit. Rev. Clin. Lab. Sci. 21:187-228, (1984); Peacock, J. Clin. Pathol. 37:841-851, (1984); Miedema et al., Ann. Clin. Biochem. 21:2-15, (1984); Mayer et al., Clin. Chem. Acta 127:147-184, (1983); Gabbay, Med. Clin. North Am. 66:1309-1315, (1982). The concentration of hemoglobin A1c is recognized as being directly related to time-averaged blood glucose levels and is correlated with various stages of metabolic control in diabetic patients.

Normal, non-diabetic patients have a HbA1c level of between about 4-8% of total hemoglobin, while the HbA1c level in diabetic patients may range up to about 15% of total hemoglobin. Hypoglycemic patients correspondingly have a HbA1c level below about 3% of total hemoglobin. Various clinical methods have been developed to provide practical means for assessing the HbA1c level in a sample of a patient's blood, with detection levels of 3-20% HbA1c. Such methods include both electrophoretic and chromatographic techniques. In both electrophoretic and chromatographic methods, standards and control materials having known glycosylated hemoglobin concentrations are necessary in order to assure day-to-day consistency of test results and to provide a reference for calibration of equipment.

Hospital labs and clinics are required to operate in compliance with state and federal regulations. The International Federation of Clinical Chemistry Working Group (IFCC-WG) on HbA1cStandardization has developed reference methods for HbA1c analysis. They have established a laboratory network, which includes two reference methods, i.e., mass spectroscopy and capillary electrophoresis. Each network laboratory uses prepared mixtures of purified Hemoglobin A1c and HbA0 as calibrators. The relationship between HbA1c results from the National Glycohemoglobin Standardization Program (NGSP) network and the IFCC network has been evaluated. The NGSP system was established after the Diabetes Control and Complications Trial (DCCT) study showed the relationship between $HbA_{1c}$ and risks for development and/or progression of diabetes complications. See, e.g., *Clinical Chemistry* 50: 166-174, 2004; 10.1373/clinchem.2003.024802.

Many insurance and Medicare reimbursement programs require that labs be accredited through organizations such as the College of American Pathologists or the American Proficiency Institute. Such accrediting agencies recommend the use of quality controls to verify that an in vitro diagnostic medical device is operating properly. Diagnostic devices such as compact portable devices intended for satellite and point of care settings (including home use) are also subject to similar regulations, such as for example, the devices described in U.S. Pat. No. 5,580,794 and U.S. Pat. No. 5,837,546, the contents of both of which are incorporated herein in their entireties by reference.

In order to make possible a precise determination of the concentration(s) of analyte(s) in a sample solution, a comparison is made with a calibration curve that has been produced/prepared using standard solutions having known concentrations of analytes. Furthermore, for the precision control of the method of determination and for the calibration of automatic analyzers, it is necessary to use standard solutions with known content. Standard solutions that are used for this purpose preferably contain the measurement parameter to be determined in known concentration. The concentration of the parameter ideally lie in the medically relevant measurement range. The handling of the standard solutions is preferably relatively simple. Such standards should also have a storage stability which is as long as possible for obvious practical reasons. In particular, in the case of compact diagnostic devices, such standard controls should ideally have a suitable room temperature stability. The hitherto known standard solutions for HbA1c determinations do not fulfill several of these prerequisites.

Several instruments currently available combine the measurement of blood pH, glucose, ketone, microalbumin, creatine, urea and markers of proteinuria, gases, electrolytes, as well as various other metabolites in one instrument for a comprehensive testing of the patients tissues. Before such tests can be performed, however, the chemistry analyzer being used must be also be calibrated for these additional analytes to ensure that it is functioning properly. At the present time, laboratories routinely perform multiple calibrations to assess reliability and accuracy as to each individual analyte. These separate steps entail repeated accurate pipetting steps and are costly, time-consuming, labor intensive procedures requiring skilled technicians. There is a definite need for a simple, rapid, accurate assay which can be performed by unskilled users. It is toward the fulfillment of this need that this disclosure is directed.

Additionally, at the present time HbA1c quality controls generally require reconstitution or multiple inversion to resuspend fixed red blood cells. These preparations are not only technique sensitive but also time consuming. Furthermore, prior liquid or reconstituted dry control materials are generally turbid, contain particulate matter, and/or have low shelf lives. Turbidity is generally caused by the presence of lipids or cell stroma. Also, prior controls sometimes contain preservatives in order to enhance shelf life. Such preservatives are generally undesirable because they bind with or dissociate the hemoglobin molecule, or otherwise adversely affect hemoglobin present in the control material. Frequently, reconstitution steps are performed improperly and must be repeated. Some hospital labs are required to perform QC cross over studies when they switch to a new lot, therefore having a product with long shelf life reduces the workload. Additionally, since many new analyzers are portable and have room temperature stable cartridges, they are being located in Point of Care or Physicians' offices. These setting do not have much refrigeration space, so a control with room temperature stability is desirable.

Presently, most hemoglobin controls utilize human or bovine hemoglobin moieties (see e.g., Bionostics FDA 510k, K050961 RNA1C CONTROL FOR NYCOCARD HBA1C). There can be several disadvantages in implementation of such controls. A well recognized problem lies in the difficulty to identify non-hazardous preservatives to bind to the protein that also effectively kill microbes. For example, as disclosed in Fiechtner, U.S. Pat. No. 5,589,393, a method of preparing a refrigerated glycated hemoglobin solution required the use of sodium azide and sodium cyanoborohydride, which are known to be hazardous and dangerous materials. Second, such human or bovine hemoglobin controls are problematic in that glucose naturally binds to the hemoglobin and forms HbA1c. Consequently, analyzer controls that utilize human or bovine hemoglobin cannot be formulated to include both glucose and hemoglobin.

Investigators seeking to overcome these limitations have sought to use modified forms of hemoglobin. Many such efforts have lead to compositions that have proved to have absorption characteristics dissimilar to natural hemoglobin, or which are prone to oxidation and are thus, unstable at room temperature.

Others have devised Hb control solutions relying on relatively large molecular weight Hb peptides. Such controls have been shown to present binding problems, as well as insurmountable room temperature stability issues. For example, a large molecular weight peptide begins to resemble to native molecule. Examples of large molecular weight HB peptides can be found in commercially available blood substitutes such as made available by BioPure Corporation of Boston, Mass., USA, under the name Hemopure® blood substitute (hemoglobin glutamer—250—bovine), or HBOC-201 (cross linked hemoglobin).

Thus, there is a need in the art for Hb standard control solutions that avoid the use of hazardous materials, rely on Hb peptides having a relatively low molecular weight, and which are also stable at room temperature (see e.g., Bionostics FDA 510k, K050100 RNA1C HEMOGLOBIN A1C CONTROL FOR BAYER DCA2000 ANALYZER).

In addition, there is also a need for a comprehensive standard control to provide a single reliable reference suitable for the simultaneous calibration of devices used for the measurement of multiple analytes including glycated hemoglobin. To address the shortcomings of presently available products, such a versatile standard should (a) be based on the inclusion of a hemoglobin peptide moiety that is stable at room temperature and does not interfere with the simultaneous calibration for other analytes recurrently tested in the management of diabetes; and (b) be devoid of hazardous material.

SUMMARY OF DISCLOSURE

Embodiments of the present disclosure provide standard references useful to the quality control testing and calibration of chemistry analyzers used in the detection and monitoring of analytes of interest, including analytes that are routinely evaluated in the diagnosis and management of diabetes and diabetes related conditions. Such novel standard references are based on materials that are stable at room temperature and that do not interfere with the concurrent calibration of various analytes of interest in the context of diabetes management including blood cell analytes (primarily, glycated hemoglobin), plasma analytes (e.g., glucose and ketone), and urine analytes (e.g., microalbumin and creatine). Such standard references can provide the added benefit of not requiring the inclusion of hazardous materials often found in standard reference materials currently used in the field.

Embodiments of the disclosure can provide standard reference compositions that include a synthetic cruor and an Hb peptide chain, as well as related methods for their preparation and use. As described herein, the synthetic cruor can be a moiety spectrally equivalent to human hemoglobin.

In exemplary embodiments according to the present disclosure, the standard reference compositions (and methods for their preparation and use) can include a Hb peptide chain comprises from about 3 to about 50 amino acids. Such Hb peptide chains may be subject to glycosylation, lipidation, and/or phosphorylation as further discussed infra.

Embodiments may be utilized to provide such standard reference compositions and methods suitable for the quality control testing and calibration of systems that analyze the ratio of glycated hemoglobin, hemoglobin A1c, and additional variants including, e.g., HbA1, HbA2, HbC, HbF, and HbS.

Additionally, embodiments of this disclosure may be utilized to provide comprehensive standard reference compositions and methods for their preparation and use suitable for the quality control testing and calibration of systems that analyze multiple analytes of interest in the context of diabetes management including blood cell analytes (primarily, glycated hemoglobin), plasma analytes (e.g., glucose and ketone), and urine analytes (e.g., microalbumin and creatine).

BRIEF DESCRIPTION OF THE DRAWINGS

Aspects of the disclosure may be more fully understood from the following description when read together with the accompanying drawing, which is to be regarded as illustrative in nature, and not as limiting.

It should be understood by one skilled in the art that the embodiments depicted in the drawings are illustrative and variations of those shown as well as other embodiments described herein may be envisioned and practiced within the scope of the disclosure.

DETAILED DESCRIPTION OF THE DISCLOSURE

Embodiments of the present disclosure are directed to advantageous standard reference compositions suitable for diagnostic medical devices and/or methods. Such standard reference compositions can be based on a synthetic cruor moiety mimicking hemoglobin with respect to spectral properties associated with hemoglobin found in blood, and on an Hb peptide relied upon as the glycated hemoglobin reference. In its simplest form, the disclosure provides standard reference solutions for the calibrations of devices with respect to glycated hemoglobin. Taking advantage of the versatile biochemical properties of such solutions, the disclosure also sets forth complex standard reference solutions enabling the calibration of numerous analytes in addition to hemoglobin and glycated hemoglobin.

The term "standard reference composition" is used herein to denote a composition suitable for diagnostic medical devices and related quality controls and/or calibration verification control. Accordingly, such standard reference compositions according to the present disclosure may also be referred to as controls, calibrators, standards, references, and alike terms commonly used in the field of clinical diagnostics. Standard reference compositions for use in assays according to the disclosure are preferably liquid, in exemplary embodiments.

Traditionally the word cruor meant coagulated blood. The term has also been used to designate colloidal air-entrapping agents comprising whole blood, corpuscles, erythrocytes, and hemoglobin. For the purposes of the present disclosure, the term "synthetic cruor" is used to designate a moiety mimicking total hemoglobin.

A considerable challenge overcome by the present disclosure relates to (a) the identification of those fundamental properties necessary in a synthetic cruor to arrive at the versatile compositions of the disclosure; and (b) the identification of those moieties possessing such properties. As those of skill in the art will appreciate, the challenge was ultimately tackled by a comprehensive analytical approach which led investigators to identify the required properties cumulatively. A number of dye moieties and mixes of dye moieties with the target absorbance range approximating hemoglobin have been found to fail to mimic hemoglobin analytically. Many moieties tested have been found to be incompatible with peptide preparations.

In some instances, such compounds destabilized co-formulated peptides and other co-formulated biochemical and chemical species (e.g., by precipitation, degradation, or simply by chemical interaction). In some cases, candidate compounds have been found to be incompatible with a variety of analytes of interest for inclusion in a multi-analyte composition (e.g., glucose, ketone, or creatinine) and/or with required pH values. In some instances, candidate cruors were found to decrease the overall stability of various compositions of interest according to the disclosure.

Synthetic cruors according to the present disclosure include moieties that can mimic the 560 nm hemoglobin absorbance of light and are stable at room temperature, do not interfere with the determination of other analytes included in the same composition, do not destabilize other analytes, and are compatible for inclusion in composition within required pH ranges. For an description of such pH ranges, see The Sigma-Aldrich Handbook of Stains, Dyes and Indicators by Floyd J. Green ISBN 0-941633-22-5. Hence, suitable cruors preferably have a maximum absorbance of light at a wavelength in the range between about 400 nm to about 800 nm. Typically, the synthetic cruors according to the disclosure are present in a concentration range of between 0.01 g/L to about 10 g/L. These synthetic cruors may be present in other concentrations.

Representative non-limiting examples of suitable synthetic cruors can include sulforhodamine B (which is commercially available from Sigma Aldrich), Congo Red, Mito Red, Acid Red, Fluorescent Red, Allura Red, Cresol Red. Amaranth, chlorophenol red, xylenol orange, and sulforhodamine 101, sulforhodamine red, or mixes of dyes and derivatives thereof may also be utilized. In a exemplary embodiment exemplified herein, the synthetic cruor is sulforhodamine B.

As used herein, the terms "Hb peptide chain" and "Hb peptide" denote a peptide comprising from about 3 to about 50 amino acids having <0.08% homology with the sequence of hemoglobin.

One of skill in the art will appreciate that the specific sequence will depend on the specific glycated hemoglobin moiety variant being calibrated, such as for example hemoglobin A1c, and all known variants, including but not limited to HbA1, HbA2, HbC, HbF, and HbS. In exemplary embodiments of the disclosure, the Hb peptide sequence can be homologous to the hemoglobin beta chain amino acid sequence UniProtKB/Swiss-Prot P68871. According to exemplary embodiments, suitable Hb peptide chains ca comprise from about 3 to about 50 amino acids derived from SEQ. ID. NO P68871:

```
VHLTPEEKSA VTALWGKVNV DEVGGEALGR LLVVYPWTQR
FFESFGDLST

PDAVMGNPKV KAHGKKVLGA FSDGLAHLDN LKGTFATLSE
LHCDKLHVDP

ENFRLLGNVL VCVLAHHFGK EFTPPVQAAY QKVVAGVANA
LAHKYH
```

In certain embodiments, the Hb peptide chain can comprise from about 3 to about 15 (or more) amino acids. In other embodiments, the Hb peptide chain can comprise from about 3 to about 10 amino acids. Thus, in certain embodiments, the Hb peptide is a hexapepetide having the sequence Val-His-Leu-Thr-Pro-Glu. In yet other embodiments, the Hb peptide chain comprises 5 amino acids. As illustrated in Example 1, the Hb peptide chain has the sequence Val-His-Leu-Thr-Pro.

Hb peptides according to the present disclosure include Hb peptidomimetics which mimic glycated hemoglobin. An Hb peptidomimetic is a small protein-like chain (a peptide) that contains both natural and non-natural amino acids. Hb peptidomimetic moieties contemplated include those approximating the pentapeptide and hexapeptide species described infra.

Figure 1:
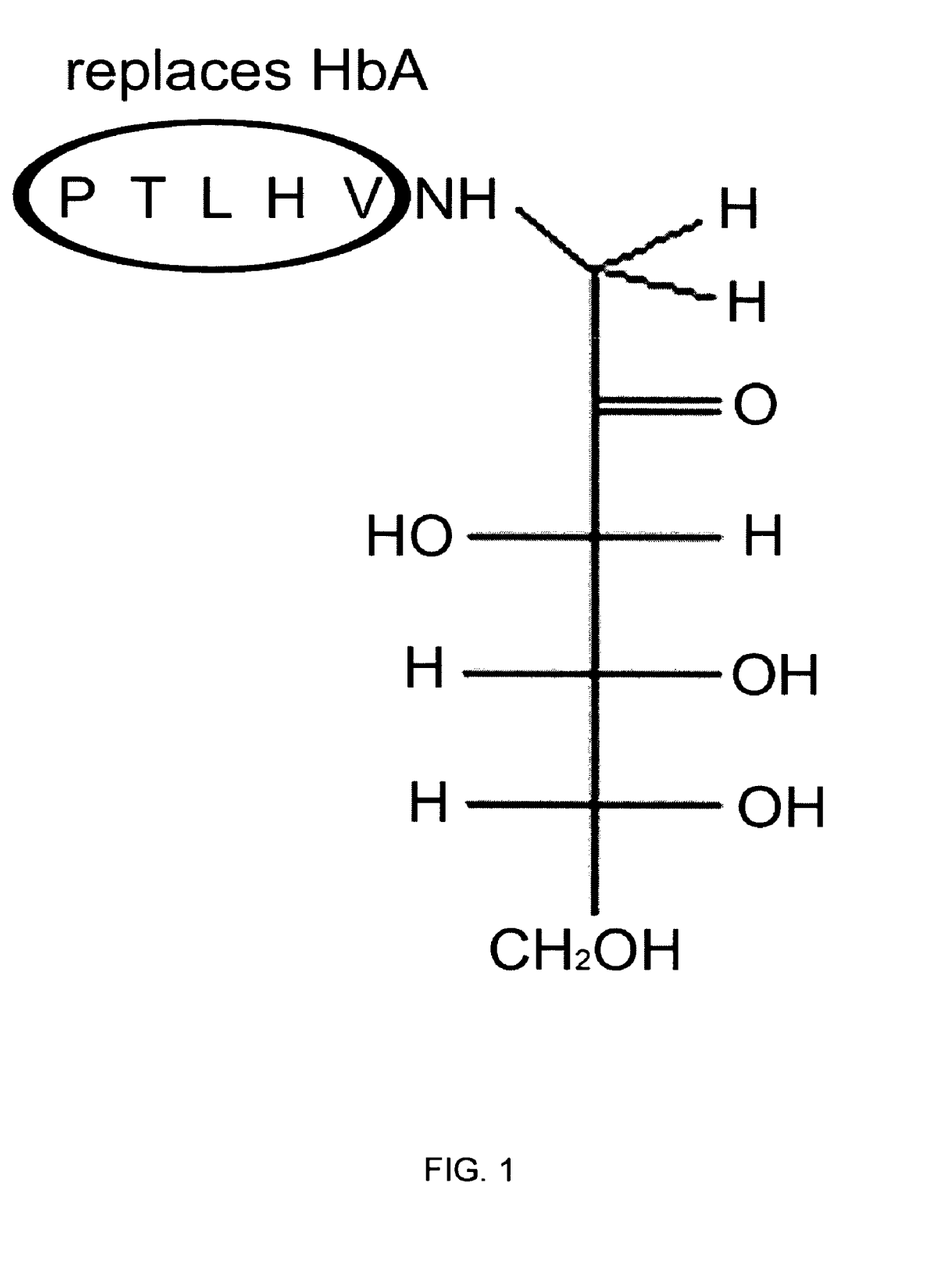
FIG. 1 shows a representative glycated peptide according to the disclosure. As shown, in the representative pentapeptide (Val-His-Leu-Thr-Pro) the Val residue was glycated mimicking hemoglobin glycation.

Hb peptide chains according to the disclosure may be further modified chemically (e.g., glycated, phosphorylated or lapidated). As shown in FIG. 1, in the representative pentapeptide (Val-His-Leu-Thr-Pro), the Val residue was glycated, mimicking hemoglobin glycation found in nature. In general, these types of peptides are not stable and water and are stored in a dessicator.

Hb peptides according to the disclosure may be derived from biological sources according to standard methods known in the field of molecular biology or may be synthesized according to standard methods known in the field of protein chemistry (see e.g., Example 1 infra). Thus, certain compositions of the disclosure may be based exclusively on non-biological components.

The adjectives "non-biological" and "synthetic" are used herein to mean that the subject component was not derived from a biological source such as for example by enzymatic digestion and size selection of native human hemoglobin. The use of non-biological/synthetic components virtually eliminates the risk of contaminants including pathological contaminants (e.g., HIV, hepatitis, mad cow disease, etc.), and can provide consistency by eliminating variations due to the heterogeneous nature of biologically derived materials—e.g., enzymatically derived hemoglobin peptides are often a heterogeneous population—, and by eliminating those due to lot-to-lot variations associated with presently available compositions based on pooling of donor tissue samples. Also, non-biological preparations do not require the inclusion of antimicrobial hazardous materials (e.g., sodium azide) found in presently available reference materials relying on higher molecular weight bovine/ovine or human hemoglobin peptides. As discussed hereinafter, safer preservatives which may not be effective antimicrobials may be used in lieu of the more toxic ones.

To preserve the integrity of biological components currently available calibrators are generally lyophilized and thus require reconstitution and/or use fixed cell preparations and even hemoglobin which require inversion and resuspension of cells and free hemoglobin providing an added opportunity for errors and consequently inconsistent analytical outcomes. Compositions of the disclosure need not be lyophilized and do not require reconstitution or resuspension of cells eliminating these added opportunities for errors as well as time and costs requirements.

As mentioned previously, embodiments of the present disclosure can be stable at room temperature because the pH, dye and glucose concentrations have been optimized to prevent degradation of the peptide.

Presently available glycated hemoglobin calibrators are designed to calibrate analytical devices only with respect to glycated hemoglobin and total hemoglobin. Consequently, multiple protocols are routinely performed to ensure quality control and calibration verification control of in vitro diagnostic medical devices used for the determination of multiple analytes in addition to glycated hemoglobin. A considerable obstacle to the formulation of a single complex calibrator encompassing the calibration of glycated hemoglobin stems from the natural propensity of larger hemoglobin peptides to bind to glucose. Traditionally calibration approaches have relied on the inclusion of biologically-derived hemoglobin moieties (e.g., bovine, ovine or human derived) which are only partially glycated and which therefore bind glucose. Accordingly, such calibrators could not combine glucose in a single composition. In addition, as discussed above most currently available calibrators require the inclusion of hazardous antimicrobials, are inherently unstable at room temperature, and have a limited shelf life. The instant disclosure addresses and solve the underlying problems.

The fully glycated peptide moieties according to the disclosure have no affinity for glucose (since they are already fully glycated) and for the preservatives used. Compositions based on such Hb peptides provide the opportunity to combine in a single complex preparation components suitable for the calibration of device with respect to multiple analytes in addition to total hemoglobin and glycated hemoglobin.

Current manufacturers of HbA1c controls do not combine HbA1c calibration with the calibration of analytes (other than glucose) because they are using biological hemoglobin matrices.

As it may be readily apparent in light of the description of the disclosure, such complex multi-analytes standard reference compositions may be formulated with respect to one or more additional analyte in addition to glycated hemoglobin/hemoglobin. Accordingly, the present disclosure provides standard reference compositions and methods useful for the quality control testing and calibration of devices used in the detection and monitoring of multiple analytes of interest. Additional analytes of particular interest are those medically involved in the diagnosis and management of diabetes and diabetes related conditions.

In some embodiments analytes of interest include those of relevance in monitoring the concentration of a given drug administered to a patient including but not limited to drugs routinely administered in the management of diabetes and diabetes related conditions (see generally Goodman and Gilman's *The Pharmacological Basis of Therapeutics*, 10$^{th}$ Ed., McGraw Hill Companies Inc., New York (2001)) e.g., insulin. On the other hand, complex multi-analytes standard reference compositions may encompass a variety of analytes of interest which may not be necessarily related to diabetes and/or related conditions.

Thus, as utilized herein the term "analyte" denotes any material of interest. Analytes of interest may include, but are not limited to, glucose, cholesterol (high density, low density and total cholesterol), tryglycerides, fructosamine, amino acids, electrolytes ($Na^+$, $K^+$, and $Cl^-$), urea, uric acid, lactate, ketones, ketone bodies (acetoacetate and 3-hydroxybutyrate), hemoglobin, glycosylated hemoglobin, microalbumin, creatine, creatinine, metabolites related to disease, drugs and drug metabolites, pesticides, haptens and antigens (e.g., components of peptides, proteins, polysaccharides, nucleic acids, bacteria, viruses, chromosomes, genes, mitochondria, nuclei, cell membranes, and the like), and antibodies.

Drugs of interest as analytes include alkaloids, steroids, lactams, aminoalkylbenzenes, benzheterocyclics, purines, vitamins, prostaglandins, antibiotics, nucleosides, nucleotides, aminoglycosides, cannabinol and tetrahydrocannabinol. Alkaloids include morphine alkaloids (e.g., morphine, codeine, heroin, and dextromethorphan), cocaine alkaloids (e.g., cocaine and benzoyl ecgonine), ergot alkaloids (e.g., diethylamide of lysergic acid), steroid alkaloids, iminazoyl alkaloids, quinazoline alkaloids, isoquinoline alkaloids, quinoline alkaloids (e.g., quinine and quinidine), diterpene alkaloids, and their derivatives and metabolites. Steroid analytes include estrogens, estogens, progestogens, androgens, andreocortical steroids, bile acids, cardiotonic glycosides and aglycones (e.g., digoxin and digoxigenin), saponins and sapogenins, and their derivatives and metabolites. Steroid mimetic substances, such as diethylstilbestrol, are also drug analytes of interest. Lactam analytes include barbituates (e.g., phenobarbital and secobarbital), diphenylhydantonin, primidone, ethosuximide, and their derivatives and metabolites. Aminoalkylbenzenes analytes include amphetamines, catecholamines (e.g., ephedrine, L-dopa, epinephrine, narceine, papaverine), and their derivatives and metabolites. Benzheterocyclic analytes include drugs that have an azepine, diazepine or phenothiazine heterocyclic ring compounds, such as oxazepam, chlorpromazine, tegretol, imipramine, and their derivatives and metabolites. Purine analytes include theophylline, caffeine, and their derivatives and metabolites. Vitamin analytes of interest include A, B, $B_{12}$, C, D, K, folic acid and thiamine. Antibiotic analytes include penicillin, chloromycetin, actinomycetin, tetracycline, teramycin, and their derivatives and metabolites. Nucleoside and nucleotide analytes include adenosine triphosphate (ATP), nicotinamide adenine dinucleotide (NAD), flavin mononucleotide (FMN), adenosine, guanosine, thymidine, and cytidine, and their derivatives and metabolites. Other drug analytes of interest include methadone, meprobamate, serotonin, meperidine, amitriptyline, nortriptyline, lidocaine, procaineamide, acetylprocaineamide, propanolol, griseofulvin, valproic acid, butyrophenones, antihistamines, anticholinergic drugs (e.g., atropine), and their derivatives and metabolites. Metabolites related to disease states which may be analytes of interest include spermine, galactose, phenylpyruvic acid, and porphyrin. Pesticides of interest include polyhalogenated biphenyls, phosphate esters, thiophosphates, carbamates, polyhalogenated sulfonamides, and their derivatives and metabolites.

In exemplary embodiments, the analyte can be glucose. Generally, glucose may be present in a solution of the disclosure in a concentration range of between about 10 mg/dL to about 500 mg/dL. In another exemplary embodiment, the analyte is microalbumin. Generally, microalbumin is present in a solution of the disclosure in a concentration range of between about 0.05 mg/dL to about 70 mg/dL. In yet another embodiment of the disclosure, the analyte is a ketone species. Generally, the ketone is present in a solution of the disclosure in a concentration range of between about 0 mMol/L to about 10 mMol/L. In some embodiments, the analyte is creatine. Generally, creatine is present in a solution of the disclosure in a concentration range of between about 30 mg/dL to about 400 mg/dL. In some instances, the analyte is creatinine. Generally, creatinine is present in a solution of the disclosure in a concentration range of between about 0.3 mg/dL to about 265 mg/dL.

Non limiting representative examples of standard multi-analytes reference compositions with concentrations according to the present disclosures are shown in Table 1 infra.

TABLE 1

| Chemical | Amount/Concentration |
| --- | --- |
| HEPES | 9.5 g/L |
| Sodium Chloride | 5.5 g/L |
| Sodium Hydroxide | 1.08 g/L |
| DiSodium EDTA 2H2O | 0.5 g/L |
| Sulforhodamine B | 0.008 g/L |
| Synthetic Peptide | 0.0005 to .0015 g/L |
| Recombinant Human Serum Albumin | 0.219 to 1.537 g/L |
| DL-β-Hydroxybutyric Acid | 0.25 to 1.123 g/L |
| Creatinine | 0.31 to 2.61 g/L |
| Creatine | 0.465 to 3.915 g/L |
| D-Glucose | 0.85 to 2.80 g/L |

Standard reference compositions according to the present disclosure may also include a buffer to maintain the pH. Standard reference compositions of the disclosure have a pH in the range of between about 4.0 to about 9.0. Preferably, the pH is maintained within the pH range of about 5.0 to about 7.5 (e.g., see Example 3 providing a final pH of 7.48). In a exemplary embodiment, the buffer can include a N-2-hydroxyethyl-piperazine-N-2-ethanesulfonic acid (HEPES) and or a citrate buffer, as well as all buffers listed in Buffers for pH and Metal Ion Control written by DD Perrin, Boyd Dempsey ISBN: 0470680679 Publisher: Wiley (1974) This buffer is typically used when it is desirable to maintain the pH of the control solution within a range of about 4 mmol/L to about 100 mmol/L.

One or more preservatives may be used in the standard reference compositions in accordance with the present disclosure. A preservative is a compound that inhibits the growth of bacteria in the solution, such as antibiotics (e.g., streptomycin, gentamycin), sodium benzoate, potassium benzoate, benzalkonium chloride, chlorhexidine, imidazolidinyl urea, diazolidinyl urea (also called Germall II), 5-chloro-2-methyl-4-isothiazolin-3-one, and 2-methyl-4-isothiazolin-3-one. Exemplary preservatives are diazolidinyl urea, 5-chloro-2-methyl-4-isothiazolin-3-one, and 2-methyl-4-isothiazolin-3-one or a mixture thereof. An exemplary preservative is a mixture of 5-chloro-2-methyl-4-isothiozalin-3-one (2.3%), 2-methyl-4-isothiazolin-3-one (0.7%), plus inert ingredients modified glycol (93-95%) and alkylcarboxylate (2-3%), known collectively as ProClin 300. When a preservative is present in a control solution of the disclosure, it is typically present in a concentration range of between about 0.5 g/L to about 2.0 g/L.

One or more chelators may be added to preserve the integrity of the various components, or to inhibit microbial contamination of the compositions of the disclosure. A "chelator" is an organic compound the atoms of which form more than one coordinate bond with one or more metal. Chelators are well known in the art including for example, ethylenediaminetetraacetic acid (EDTA), citric acid, and salts thereof. Salts of chelators can be formed in the same manner as salts of surfactants having an acidic group. When a chelator is present in a control solution of the disclosure, it is typically present in a concentration range of between about 0.01 mM to about 100 mM.

One of skill in the art will appreciate that depending on the analytes of interest and the particular exigencies presented by the overall formulation including such analytes, standard reference solutions according to the disclosure may also contain surfactants, antifoaming agents, viscosity enhancers, and/or suitable detergents or emulsifiers. Many buffers, preservatives and chelators in addition to those specifically named as well surfactants, antifoaming agents, and viscosity enhancers are well known in the art and are contemplated for inclusion in the compositions according to the disclosure (see e.g., *Remington's Pharmaceutical Sciences*, 18$^{th}$ Ed., Gennaro, Mack Publishing Co., Easton, Pa. 1990 and *Remington: The Science and Practice of Pharmacy*, Lippincott, Williams & Wilkins, 1995.

The standard reference solutions and methods of the present disclosure are useful for quality control testing and calibration of in vivo and in vitro medical instruments and devices such as those found in clinical laboratories, clinics, physicians offices and alike as well as compact portable diagnostic/monitoring devices intended for satellite and point of care settings (including home use).

Further provided herein are methods of calibrating an instrument using the compositions according to the disclosure as described supra.

The standard reference solutions of the disclosure may be used in a variety of methods for quality control testing and calibration of devices. Such methods are well established in the field which may be especially adapted to meet the particular exigencies as necessary for any particular devices. In certain embodiments, the disclosure provides a method of quality control of a device by providing an aliquot of a standard reference composition to the device being tested which includes predetermined amounts of a synthetic cruor and an Hb peptide as described above, quantitating the synthetic cruor and an the Hb peptide and comparing the quantitations derived from the device being tested with the predetermined amounts of each analyte.

Further embodiments of the present disclosure can provide a method of quality control of a device by providing an aliquot of a standard reference composition to the device being tested which includes a predetermined fraction of synthetic cruor/Hb peptide as described above, quantitating the fraction of synthetic cruor/Hb peptide, and comparing the quantitations derived from the device being tested with the predetermined fraction. In other embodiments, the methods of the disclosure may comprise use of additional analytes (as discussed above).

In the specification and the appended claims, the singular forms include plural referents unless the context clearly dictates otherwise. As used in this specification, the singular forms "a," "an," and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of "either/or." As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

Technical and scientific terms used herein have the meaning commonly understood by one of skill in the art to which the present disclosure pertains, unless otherwise defined. Reference is made herein to various methodologies and materials known to those of skill in the art. Standard reference works setting forth the general principles of clinical diagnostics include for example Bishop et al., *Clinical Chemistry Principles, Procedures, Correlations*, 2$^{nd}$ Ed., J. B. Lippincott Company, Philadelphia (1992). Standard reference works setting forth the general principles of recombinant DNA technology include Sambrook et al., *Molecular Cloning: A Laboratory Manual*, 2$^{nd}$ Ed., Cold Spring Harbor Laboratory Press, New York (1989); Kaufman et al., Eds., *Handbook of Molecular and Cellular Methods in Biology in Medicine*, CRC Press, Boca Raton (1995); McPherson, Ed., *Directed Mutagenesis: A Practical Approach*, IRL Press, Oxford (1991).

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The present disclosure will be further understood by reference to the following non-limiting examples. The various applications and processing shown here are exemplary only. Those skilled in the art will appreciate that modifications can be made to these examples within the scope of the present disclosure.

EXAMPLE 1

Preparation of Glycated VHLTP Peptide

The instant example illustrate the synthesis and glycation of a representative pentapeptide according to the disclosure.

Synthesis of a pentapeptide was accomplished through the use of a combination of Solid Phase synthesis, Biomolecule Conjugation, Solution Phase synthesis Boc-peptide resin cleavage protocol, and a Fmoc-peptide resin cleavage protocol. One of skill in the art will appreciate that one or more suitable derivatives may be used for such synthesis (e.g., amides, etc.).

For glycation of the pentapeptide, a Non-enzymatic method proprietary to Syn-Pep was used.

Verification of pentapeptide glycation and related data were performed through use of HPLC Mass-Spectroscopy: Hexapeptide Lot 03BI8112, Theoretical Mass=857.0 Mass Found=857.3 HPLC Purity=77.3% Pentapeptide Lot 038BI8111Theoretical Mass=728.2 Mass Found=728.0 HPLC Purity=83.7%

EXAMPLE 2

Synthetic Cruor Compositions

Synthetic cruor compositions were prepared and tested against known standards to illustrate their properties mimicking total hemoglobin preparations derived from mammalian blood (e.g., human or bovine) of known concentrations.

The ingredients for each formulation are listed in Table 2.

TABLE 2

| Synthetic Cruor Preparation (Base Solution) | |
| --- | --- |
| Chemical | Amount/Concentration |
| HEPES | 9.5 g/L |
| Sodium Chloride | 5.5 g/L |
| Sodium Hydroxide | 1.08 g/L |
| DiSodium EDTA 2H2O | 0.5 g/L |
| Sulforhodamine B | 0.008 g/L |

UV Absorbance of SRAB of the synthetic cruor preparations were tested on a Shimadzu Spectrophotometer and found to be between 0.5 and 1.5. pH tested was tested on a IL1304/1620 Blood gas analyzer and found to be 7.500.

EXAMPLE 3

Stability Testing

Stability data were collected for at least four complex standard solutions (four lots) including additional analytes in addition to HbA1c/Hb, as shown in Table 3, infra; testing to obtain these data was performed on a Cobas Mira testing apparatus.

TABLE 3

| Temp/Time | Microalbumin (mg/L) | Creatinine (mg/dL) | Hb (umol/L) | HbA1c (umol/L) | % HbA1c | BHY (Ketone) (mM) | Glucose (mg/dL) |
|---|---|---|---|---|---|---|---|
| | | | lot x40204C Level 1 | | | | |
| % Change 32° C./3 months | −2.1 | 3.4 | −1.4 | −8.6 | −5.2 | 1.1 | −3.4 |
| | | | lot x40204D Level 2 | | | | |
| % Change 32° C./3 months | −6.4 | −5.0 | 0.5 | −22.7 | −19.9 | −2.9 | −5.1 |
| | | | lot x40204C Level 1 | | | | |
| % Change 2-8° C./20 months | −2.3 | 2.2 | −5.6 | 12.9 | 13.1 | −3.7 | 4.6 |
| | | | lot x40204D Level 2 | | | | |
| % Change 2-8° C./20 months | 24.6 | 12.8 | −5.3 | 5.2 | 9.8 | −2.9 | 5.4 |

EXAMPLE 4

Complex Multi-Analytes Standard Reference Compositions

The following are representative complex multi-analytes standard reference compositions of the disclosure including hemoglobin and glycated hemoglobin determinations in addition to other analytes.

Table 4 sets forth the composition for a complex multi-analytes reference composition suitable for the calibration of a device with respect to HbA1c, MicroAlbumin, Ketone, Creatinine, and Glucose.

TABLE 4

Complex Multi-Analytes Reference Composition

| Chemical | Amount/Concentration |
|---|---|
| HEPES | 9.5 g/L |
| Sodium Chloride | 5.5 g/L |
| Sodium Hydroxide | 1.08 g/L |
| DiSodium EDTA 2H2O | 0.5 g/L |
| Sulforhodamine B | 0.008 g/L |
| Synthetic Peptide | 0.0005 to .0015 g/L |
| Recombinant Human Serum Albumin | 0.219 to 1.537 g/L |
| DL-β-Hydroxybutyric Acid | 0.25 to 1.123 g/L |
| Creatinine | 0.31 to 2.61 g/L |
| Creatine | 0.465 to 3.915 g/L |
| D-Glucose | 0.85 to 2.80 g/L |

Figure 2A:
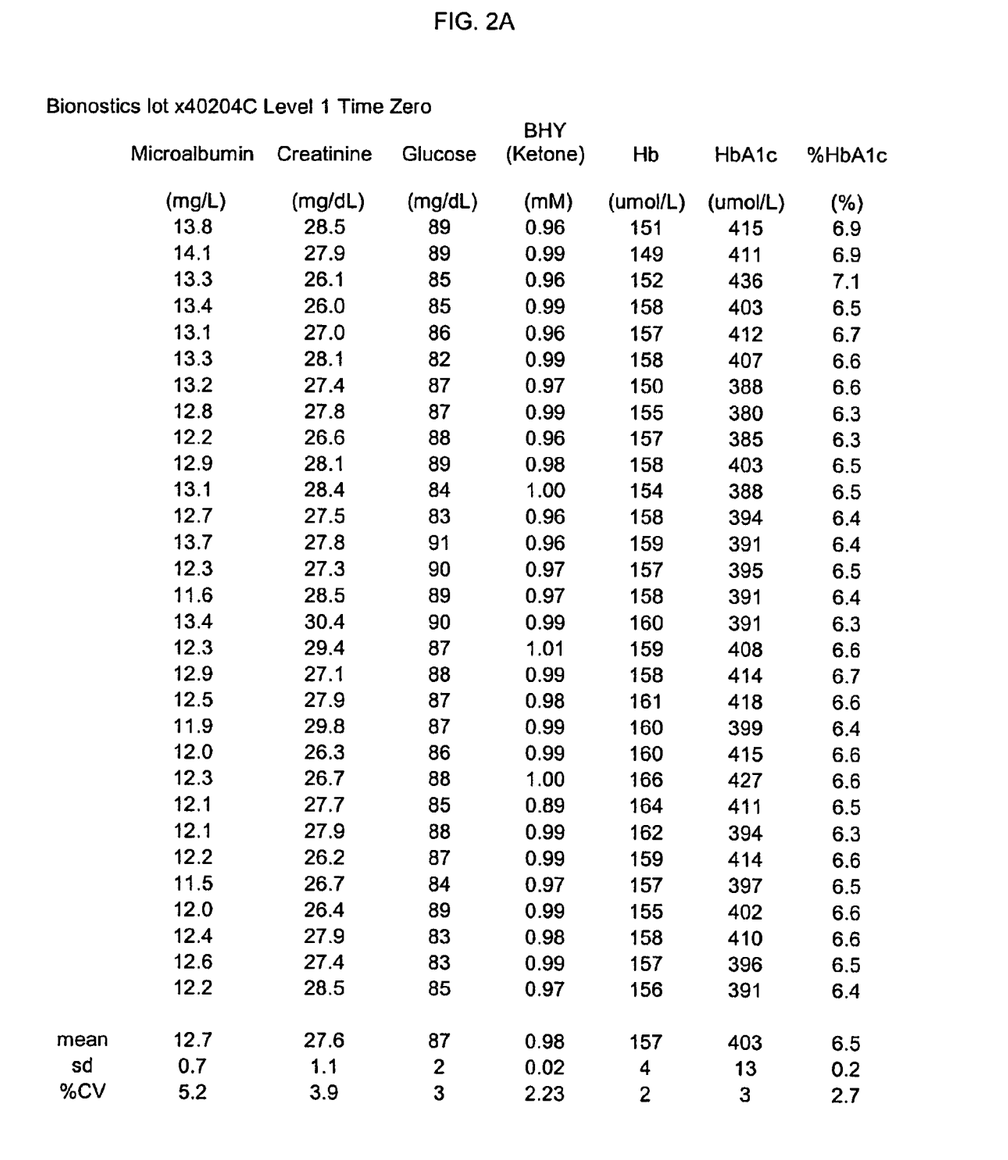
FIGS. 2A and 2B include validation data in tabular form for composition according to the present disclosure.
Figure 2B:
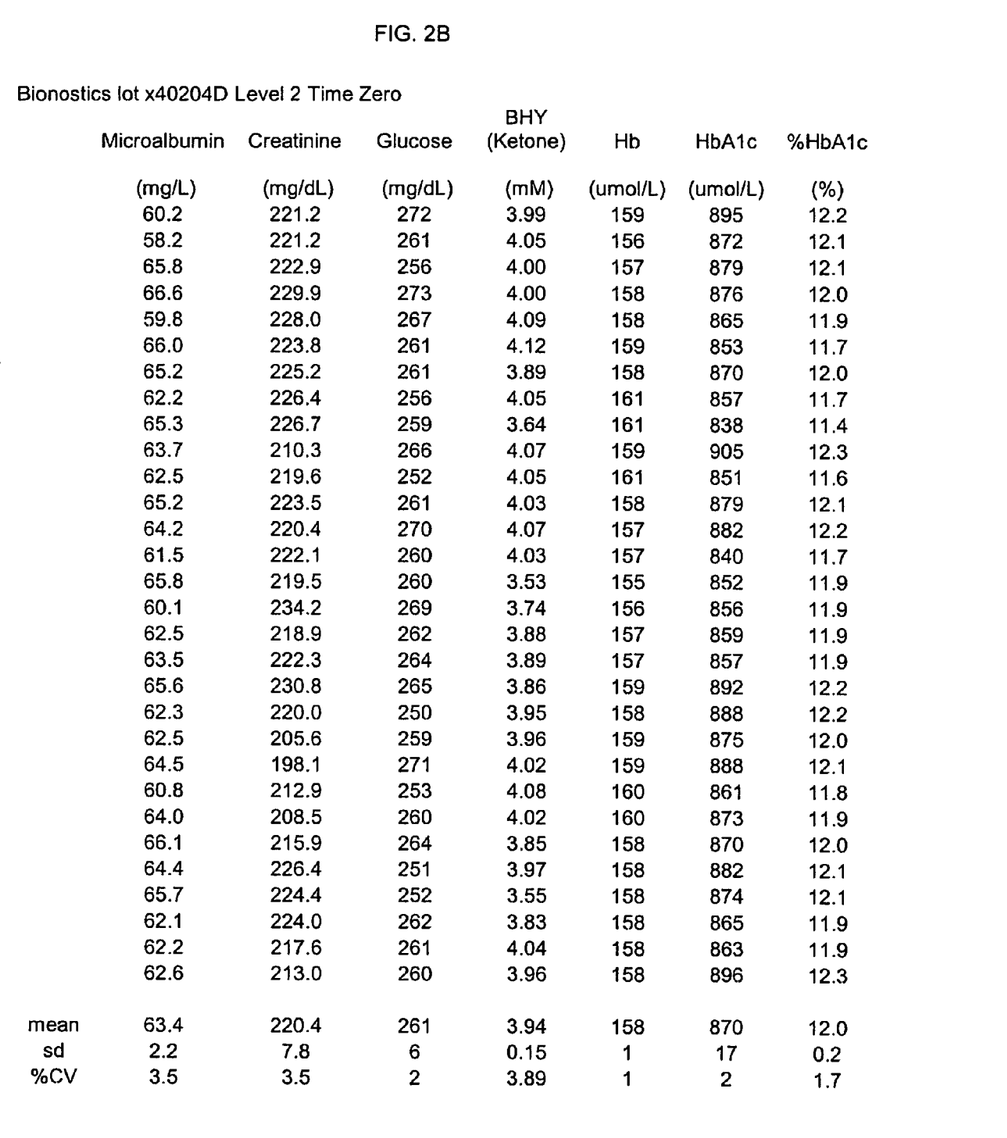

The compositions indicated in Table 4 were validated as shown in FIGS. 2A and 2B, which include validation data in tabular form for each composition respectively.

Although certain embodiments and examples have been given in previous description, it should be understood that various modifications, substitutions, and changes can be made without departing from the spirit of the present disclosure. Accordingly, the present disclosure is limited only by the appended claims.

What is claimed is:

1. A standard reference composition comprising a synthetic cruor and a synthetic Hb peptide chain, and further comprising glucose.

2. The standard reference composition of claim 1, wherein the synthetic cruor has a main absorption maxima at a wavelength between about 450 to about 650 nm.

3. The standard reference composition of claim 2, wherein the synthetic cruor is selected from the group consisting of sulforhodamine B, sulforhodamine red, Congo Red, Mito Red, Acid Red, Fluorescent Red, Allura Red, Cresol Red, Amaranth, chlorophenol red, xylenol orange, sulforhodamine 101 and combinations thereof.

4. The standard reference composition of claim 1, wherein the synthetic Hb peptide chain comprises 5 amino acids.

5. The standard reference composition of claim 4, wherein the synthetic Hb peptide chain is glycated.

6. The standard reference composition of claims 1 or 5, further comprising a preservative.

7. The standard reference composition of claim 1 or 5, further comprising a chelator.

8. The standard reference composition of claim 1, further comprising one or more analytes selected from the group consisting of microalbumin, ketone, and creatine.

9. The standard reference composition of claim 1, wherein the synthetic Hb peptide chain includes UbAI.

10. The standard reference composition of claim 9, wherein the synthetic Hb peptide chain includes HbA1c.

11. A method of quality control of a diagnostic device comprising:
providing to a diagnostic device an aliquot of a standard reference composition comprising a synthetic cruor and an Hb peptide;
wherein the synthetic cruor 15 present in a sufficient amount to provide the standard reference composition with a predetermined level of total hemoglobin, and the Hb peptide is present in a sufficient amount to provide the standard reference composition with a predetermined level of glycated hemoglobin;
quantitating in the diagnostic device the synthetic cruor in the standard reference composition;
quantitating in the diagnostic device the Hb peptide in the standard reference composition;
comparing the quantitations of the synthetic cruor and the Hb peptide in the standard reference with the predetermined amount of total hemoglobin and glycated hemoglobin to check the accuracy of the diagnostic device and wherein the standard reference composition further comprises glucose in a sufficient amount to provide the standard reference composition with a predetermined amount of glucose and further comprising the steps of:
quantitating in the diagnostic device the glucose in the standard reference composition; and
comparing the quantitations of the glucose in the standard reference with the predetermined levels of the glucose to check the accuracy of the diagnostic device.

12. A method of quality control of a diagnostic device comprising:
providing to a diagnostic device an aliquot of a standard reference composition comprising a synthetic cruor and an Hb peptide;
wherein the synthetic cruor and the Hb peptide are present in a sufficient amount to provide the standard reference composition with a predetermined fraction of Hb peptide/synthetic cruor;
quantitating in the diagnostic device the fraction of Hb peptide/synthetic cruor in the standard reference composition;
comparing the quantitation of the fraction of Hb peptide/synthetic cruor in the standard reference with the predetermined fraction of Hb peptide/synthetic cruor to check the accuracy of the diagnostic device; and
wherein the standard reference composition further comprises glucose in a sufficient amount to provide the standard reference composition with a predetermined amount of glucose and further comprising the steps of:
quantitating in the diagnostic device the glucose in the standard reference composition; and comparing the quantitation of the glucose in the standard reference composition with the predetermined levels of the glucose to check the accuracy of the diagnostic device.

13. The method of claim 11 or 12, wherein the standard reference composition further comprises an additional analyte selected from the group consisting of microalburnin, ketone, and creatine in a sufficient amount to provide the standard reference composition with a predetermined amount of the additional analyte and further comprising:
quantitating in the diagnostic device the additional analyte in the standard reference composition; and comparing the quantitation of the additional analyte in the standard reference composition with the predetermined amount of the additional analyte to check the accuracy of the diagnostic device.

14. The method of claim 11 or 12, wherein providing an aliquot of a standard reference composition comprising a synthetic cruor and an Hb peptide comprises providing an HbAI peptide.

15. The method of claim 14, wherein providing an UbAl peptide comprises providing an HbAlc peptide.

* * * * *